United States Patent [19]

Tabak et al.

[11] Patent Number: 4,751,338
[45] Date of Patent: Jun. 14, 1988

[54] CONVERSION OF DIENE-CONTAINING LIGHT OLEFINS TO AROMATIC HYDROCARBONS

[75] Inventors: Samuel A. Tabak, Wenonah; Amos A. Avidan, Mantua, both of N.J.; Fritz A. Smith, New Hope, Pa.

[73] Assignee: Mobil Oil Corporation, New York, N.Y.

[21] Appl. No.: 6,399

[22] Filed: Jan. 23, 1987

[51] Int. Cl.⁴ .............................................. C07C 12/02
[52] U.S. Cl. ...................................... 585/415; 585/533
[58] Field of Search ................................ 585/415, 533

[56] References Cited

U.S. PATENT DOCUMENTS 4,542,248 9/1985 Lucien ................................ 585/322

Primary Examiner—Curtis R. Davis
Attorney, Agent, or Firm—Alexander J. McKillop; Michael G. Gilman; L. G. Wise

[57] ABSTRACT

A technique for continuous conversion of diene-containing aliphatic hydrocarbon feedstock to heavier hydrocarbon products wherein the feedstock is contacted at elevated temperature under endothermic high severity reaction conditions with a fluidized bed of acidic zeolite fine catalyst particles, comprising methods and means for:

maintaining the fluidized catalyst bed in a vertical reactor having a turbulent reaction zone by passing vapor upwardly through the reaction zone at a velocity greater than dense bed transition velocity to a turbulent regime and less than transport velocity for the average catalyst particle;

feeding a continuous stream of feedstock into the reaction zone, said feedstream comprising sufficient $C_3^+$ alkanes to require net endothermic reaction conditions;

withdrawing a portion of coked catalyst from the reaction zone, oxidatively regenerating the withdrawn catalyst, heating the catalyst substantially above process temperature in the fluidized bed reactor, and returning hot regenerated catalyst to the reaction zone at a rate to control catalyst activity and reaction temperature under conditions of reaction severity to effect feedstock conversion to an aromatics-rich hydrocarbon effluent stream; and separating an aromatics-rich product from the fluidized bed effluent stream.

Aromatics yield is increased by recovering a recycle stream comprising $C_5^+$ aliphatic hydrocarbons from the fluidized bed effluent stream for further conversion in the fluidized bed to increase aromatics product yield.

13 Claims, 3 Drawing Sheets

CONVERSION OF DIENE-CONTAINING LIGHT OLEFINS TO AROMATIC HYDROCARBONS

BACKGROUND OF THE INVENTION

This invention relates to a catalytic technique for upgrading olefin streams rich in dienes to heavier hydrocarbons rich in aromatics. In particular, it provides a continuous process for oligomerizing a feedstock containing monoalkenes and dienes to produce $C_5+$ hydrocarbons rich in $C_6-C_{10}$ aromatics, such as benzene, toluene, xylenes, tri- and tetramethyl benzenes along with fuels and other useful products. Diene-containing liquids, such as thermal cracking liquids, are useful feedstocks herein.

Developments in zeolite catalysis and hydrocarbon conversion processes have created interest in utilizing olefinic feedstocks for producing $C_5+$ gasoline, diesel fuel, etc. In addition to basic chemical reactions promoted by ZSM-5 type zeolite catalysts, a number of discoveries have contributed to the development of new industrial processes. These are safe, environmentally acceptable processes for utilizing feedstocks that contain olefins. Conversion of $C_2-C_4$ alkenes and alkanes to produce aromatics-rich liquid hydrocarbon products were found to Cattanach (U.S. Pat. No. 3,760,024) and Yan et al (U.S. Pat. No. 3,845,150) to be effective processing using the ZSM-5 type zeolite catalysts. In U.S. Pat. Nos. 3,960,978 and 4,021,502, Plank, Rosinski and Givens disclose conversion of $C_2-C_5$ olefins, alone or in admixture with paraffinic components, into higher hydrocarbons over crystalline zeolites having controlled acidity. Garwood et al. have also contributed to the understanding of catalytic olefin upgrading techniques and improved processes as in U.S. Pat. Nos. 4,150,062, 4,211,640 and 4,227,992. The above-identified disclosures are incorporated herein by reference.

Conversion of olefins, especially alpha-monoalkenes such as propene and butenes, over HZSM-5 is effective at moderately elevated temperatures and pressures. The conversion products are sought as liquid fuels, especially the $C_5+$ aliphatic and aromatic hydrocarbons. Product distribution for liquid hydrocarbons can be varied by controlling process conditions, such as temperature, pressure and space velocity. Aromatic gasoline ($C_5-C_{10}$) is readily formed at elevated temperature (e.g., about 425° to 650° C.) and moderate pressure from ambient to about 5500 kPa, preferably about 200 to 2900 kPa. Olefinic gasoline can also be produced and may be recovered as a product or fed to a low severity, high pressure reactor system for further conversion to heavier distillate range products or otherwise utilized. Operating details for typical "MOGD" oligomerization units are disclosed in U.S. Pat. Nos. 4,456,779; 4,497,968 (Owen et al.) and 4,433,185 (Tabak), incorporated herein by reference.

Many feedstocks of commercial interest, such as thermal cracking byproduct, etc., contain both mono-olefins and diolefins (e.g. $C_2-C_6$ mono-alkenes and $C_4+$ dienes) along with light alkanes and aromatics. Gaseous and liquid streams containing dienes are typically produced in thermal cracking operations. One common example is pyrolysis gasoline which is produced as ethene (ethylene) cracking byproduct. Such diene-containing streams are often difficult to process due to poor thermal stability and the tendency of dienes to form coke and gum deposits. This complicates preheating of such streams into the high temperatures required of most catalytic upgrading processes. Prior attempts to upgrade such materials have pretreated the feedstock to hydrogenate the dienes selectively, as in U.S. Pat. No. 4,052,477 (Ireland et al). The present invention is concerned with providing a safe and low cost alternative to catalytically converting diene-rich streams to high value $C_5+$ products, rich in aromatics. The inventive process may be employed in converting paraffinic feedstocks containing diene components under endothermic reaction conditions.

It has been found that diene-containing olefinic light hydrocarbons can be upgraded directly to liquid hydrocarbons rich in $C_5+$ aliphatics and aromatics by catalytic conversion in a turbulent fluidized bed of solid acid zeolite catalyst under high severity reaction conditions without deleterious effects from the diolefin components. This technique is particularly useful for upgrading pyrolysis products, which may contain significant amounts of mono-alkenes, $C_3-C_8$ paraffins and hydrogen produced in cracking naphtha ethane or the like. By catalytically converting the cracking process by-product, aromatics production can be significantly increased. Accordingly, it is a primary object of the present invention to provide a novel technique for upgrading diene-rich olefins.

SUMMARY OF THE INVENTION

A process has been found for continuous conversion of diene-containing olefinic feedstock to heavier hydrocarbon products wherein the feedstock is contacted at elevated temperature with a fluidized bed of acidic siliceous zeolite catalyst under high severity conversion conditions to produce aromatics-rich product. The improvement is achieved by maintaining a turbulent fluidized bed of catalyst particles while flowing hydrocarbon-containing vapor upwardly through said bed at less than transport velocity; and introducing lower olefinic feedstock comprising at least one $C_4-C_6$ diene component into the fluidized catalyst bed in a lower portion thereof to convert feedstock to heavier hydrocarbon rich in aromatic liquid without substantial thermal diene degradation thereof prior to contacting conversion catalyst particles in the fluidized bed. Advantageously, the diene-containing feedstock is injected into the reactor as a pressurized liquid, with finely dispersed liquid particles being mixed rapidly and vaporized in the turbulent bed of hot catalyst. By separating an aromatics-rich liquid stream from fluidized bed reaction effluent and extracting aromatics components from the liquid stream, an aromatic product is recovered. A liquid stream rich in $C_5+$ aliphatics hydrocarbons can be recycled for further conversion in the fluidized bed reaction zone.

In a preferred embodiment of the invention, the olefinic feed comprises about 5 to 70 wt. % $C_4+$ mono-olefin, 25 to 50% $C_3$ to $C_8$ alkane, and 5 to 50 wt. % conjugated unsaturated dienes, and the fluidized bed is maintained at an average temperature of about 315 to 650 C., preferably about 425° to 510° C. The preferred catalyst comprises oxidatively regenerable medium pore shape selective metallosilicate, such as ZSM-5.

The desired products are $C_6$ to $C_9$ aromatic hydrocarbons, which will ordinarily comprise at least 50% of the recovered product, preferably 80% or more. It is desired to upgrade the feedstock to chemical products and/or higher octane gasoline containing aromatics, preferably at least 50% $C_6$–$C_8$ aromatics (BTX).

DESCRIPTION OF PREFERRED EMBODIMENTS

Description of Catalysts

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B, Fe or mixtures thereof, within the zeolitic framework. These medium pore zeolites are favored for acid catalysis; however, the advantages of ZSM-5 structures may be utilized by employing highly siliceous materials or cystalline metallosilicate having one or more tetrahedral species having varying degrees of acidity. ZSM-5 crystalline structure is readily recognized by its X-ray diffraction pattern, which is described in U.S. Pat. No. 3,702, 866 (Argauer, et al.), incorporated by reference.

The oligomerization catalysts preferred for use herein include the medium pore (i.e., about 5-7A) shape-selective crystalline aluminosilicate zeolites having a silica-to-alumina ratio of at least 12, a constraint index of about 1 to 12 and acid cracking activity (alpha value) of about 10–250, preferably about 15 to 80 based on total catalyst weight. In the fluidized bed reactor the coked catalyst may have an apparent activity (alpha value) of about 10 to 80 under the process conditions to achieve the required degree of reaction severity. Representative of the ZSM-5 type medium pore shape selective zeolites are ZSM-5, ZSM-11, ZSM-12, ZSM-22, ZSM-23, ZSM-35, ZSM-38, and ZSM-48. Aluminosilicate ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245 and 4,046,839; 4,414,423; 4,417,086; 4,517,396 and 4,542,251. The disclosures of these patents are incorporated herein by reference. While suitable zeolites having a coordinated metal oxide to silica motor ratio of 20:1 to 200:1 or higher may be used, it is advantageous to employ a standard ZSM-5 having a silica alumina molar ratio of about 25:1 to 70:1, suitably modified if desired to adjust acidity and aromatization characteristics. A typical zeolite catalyst component having Bronsted acid sites may consist essentially of aluminosilicate ZSM-5 zeolite with 5 to 95 wt.% silica and/or alumina binder.

These siliceous zeolites may be employed in their acid forms ion exchanged or impregnated with one or more suitable metals, such as Ga, Pd, Zn, Ni, Co and/or other metals of Periodic Groups III to VIII. The zeolite may include a hydrogenation-dehydrogenation component (sometimes referred to as a hydrogenation component) which is generally one or more metals of group IB, IIB, IIIB, VA, VIA or VIIIA of the Periodic Table (IUPAC), especially aromatization metals, such as Ga, Pd, etc. Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (eg, ionic $Ni^{+2}$, and a shape-selective medium pore acidic oligomerization catalyst, such as ZSM-5 zeolite) which components may be present in admixture or combined in a unitary bifunctional solid particle. It is possible to utilize an ethene dimerization metal or oligomerization agent to effectively convert feedstock ethene in a continuous reaction zone.

Certain of the ZSM-5 type medium pore shape selective catalysts are sometimes known as pentasils. In addition to the preferred aluminosilicates, the borosilicate, ferrosilicate and "silicalite" materials may be employed.

ZSM-5 type pentasil zeolites are particularly useful in the process because of their regenerability, long life and stability under the extreme conditions of operation. Usually the zeolite crystals have a crystal size from about 0.01 to 2 microns or more. In order to obtain the desired particle size for fluidization in the turbulent regime, the zeolite catalyst crystals are bound with a suitable inorganic oxide, such as silica, alumina, etc. to provide a zeolite concentration of about 5 to 95 wt. %. It is advantageous to employ a standard ZSM-5 having a silica:alumina molar ratio of 25:1 or greater in a once-through fluidized bed unit to convert 60 to 100 percent, preferably at least 75 wt %, of the monoalkenes and dienes in the feedstock in a single pass. In the description of preferred embodiments a 26% H-ZSM-5 catalyst calcined with 75% silica-alumina matrix binder is employed unless otherwise stated.

Particle size distribution can be a significant factor in achieving overall homogeneity in turbulent regime fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 32 microns. This class of fluidizable particles is classified as Geldart Group A. Accordingly, the fluidization regime is controlled to assure operation between the transition velocity and transport velocity. Fluidization conditions are substantially different from those found in non-turbulent dense beds or transport beds.

Process Operation

In this description, metric units and parts by weight are employed unless otherwise stated.

Suitable olefinic feedstocks comprises $C_4$–$C_6$ alkenes including conjugated dienes as 1,3-butadiene, pentadiene isomers, hexadienes, cyclic dienes, or similar $C_4^+$ aliphatic liquid hydrocarbons having diethylenic conjugated unsaturation. Aromatics coproduced with the liquid olefinic components may be cofed or separated by solvent extraction prior to conversion of the diene-rich feedstock. Non-deleterious components, such as $C_1$–$C_2$ lower paraffins and inert gases, may be present. A particularly useful feedstock is a liquid by-product by pyrolysis or thermal cracking units containing typically 40–95 wt.% $C_4$–$C_6$ total mono-olefins and di-olefins, including about 5–60 wt.% diene, along with varying amounts of $C_3$–$C_8$ paraffins, aromatics and inerts. Specific examples are given in the examples. The process may be tolerant of a wide range of total alkanes, from 0 to 95%. Preferred pyrolysis feedstocks may contain more than 50 wt.% $C_4$–$C_6$ lower aliphatic hydrocarbons, and contain sufficient olefins to provide a total olefinic partial pressure of at least 50 kPa. Under the high severity reaction conditions employed in the present invention, the $C_3$–$C_8$ lower alkanes are partially converted to heavier hydrocarbons.

The reaction severity conditions can be controlled to optimize yield of $C_6$–$C_8$ BTX hydrocarbons. It is understood that aromatics and light paraffin production is promoted by those zeolite catalysts having a high concentration of Bronsted acid reaction sites. Accordingly, an important criterion is selecting and maintaining catalyst inventory to provide either fresh or regenerated catalyst having the desired properties. Typically, acid cracking activity (alpha value) can be maintained from high activity values greater than 200 to significantly lower values under steady state operation by controlling catalyst deactivation and regeneration rates to provide an apparent average alpha value (base on total catalyst) below 200, preferably about 10 to 80.

In a turbulent fluidized catalyst bed the conversion reactions are conducted in a vertical reactor column by passing feedstock gas upwardly through the reaction zone at a velocity greater than dense bed transition velocity and less than transport velocity for the average catalyst particle. A continuous process is operated by withdrawing a portion of coked catalyst from the reaction zone, oxidatively regenerating the withdrawn catalyst and returning regenerated catalyst to the reaction zone at a rate to control catalyst activity and reaction severity whereby propane:propene molar ratio in the hydrocarbon product is maintained at about 0.2:1 to ..:1 under conditions of reaction severity to effect feedstock conversion.

A thermodynamically balanced mixture of exothermic alkenes and endothermic alkanes can be converted without significant recycle and/or diluent. However, a supplemental feedstream or recycle stream such as $C_3^-$ hydrocarbons can be introduced into the reactor bed. Such a recycle stream can increase $C_5^+$ aliphatic and aromatic yields, while lowering catalyst makeup requirements.

Reaction temperatures and contact time are also significant factors in the reaction severity, and the process parameters are followed to give a substantially steady state condition where the reaction severity index (R.I.) is maintained within the limits which yield a desired weight ratio of propane to propene. While reaction severity is advantageously determined by the weight ratio of propane:propene in the gaseous phase, it may also be approximated by the analogous ratios of butanes:butenes, pentanes:pentenes, or the average of total reactor effluent alkanes:alkenes in the $C_3$–$C_5$ range. Accordingly, these alternative expressions may be a more accurate measure of reaction severity conditions when propane is added to the feedstock. While this index may vary from about 0.2 to 200, it is preferred to operate the steady state fluidized bed unit to hold the R.I. below about 50, with optimum operation at 0.7 to 5 in the substantial absence of added propane. The optimal value will depend upon the exact catalyst composition, feedstock and reaction conditions; however, the typical diene-rich feed mixtures used in the examples herein and additional olefinic feeds can be optionally upgraded to the desired aliphatic-rich gasoline by keeping the R.I. at about 1.

Upgrading of olefins by such hydrogen contributors in fluidized bed cracking and oligomerization units is taught by Owen et al in U.S. Pat. No. 4,090,949. This technique is particularly useful for operation with a pyrolysis cracking unit to increase overall production of liquid product. In a typical process, the diene-rich $C_4^+$ olefinic feedstock is converted in a catalytic reactor under oligomerization conditions and moderate pressure (ie-100 to 2500 kPa) to produce a predominantly liquid product consisting essentially of $C_5^+$ hydrocarbons rich in gasoline-range mono-olefins and aromatics.

The use of fluidized bed catalysis permits the conversion system to be operated at low pressure drop, which in an economically practical operation can provide a maximum operating pressure only 50 to 200 kPa above atmospheric pressure. Another important advantage is the close temperature control that is made possible by turbulent regime operation, wherein the uniformity of conversion temperature can be maintained within close tolerances, often less than 5° C. Except for a small zone adjacent the bottom gas inlet, the midpoint measurement is representative of the entire bed, due to the thorough mixing achieved.

Figure 1:
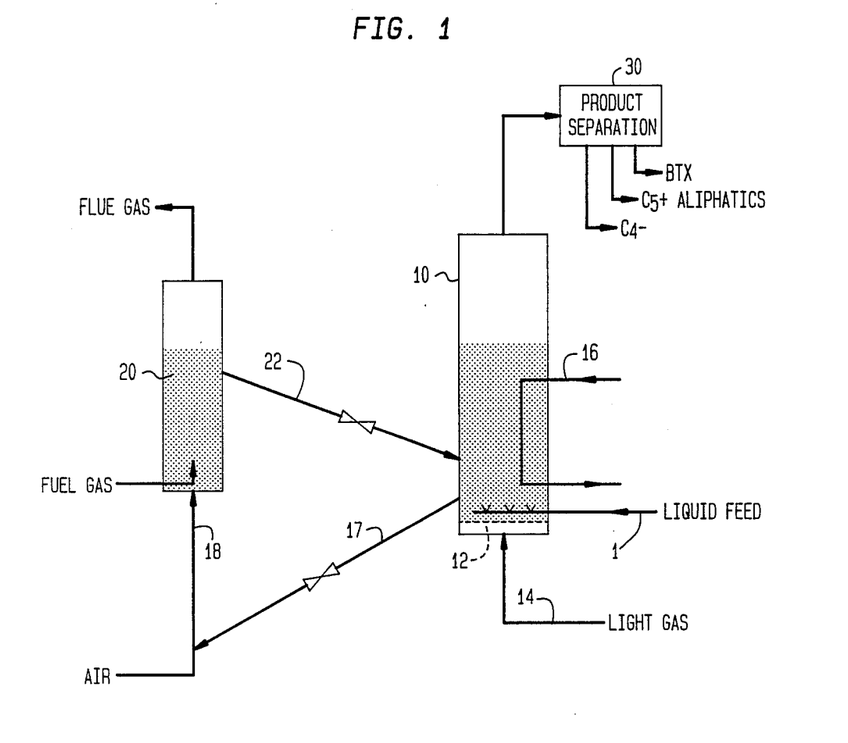
FIG. 1 is a schematic view of a fluidized bed reactor and regeneration system according to the present invention.

Referring now to FIG. 1, liquid feedstock is passed at high pressure via feed conduit 1 for injection into vertical reactor vessel 10 above a feed distributor grid 12, which provides for distribution of a lift gas passing via conduit 14 through the small diameter holes in the grid 12. Fluidization is effected in the bottom portion of the bed by upwardly flowing lift gas introduced via conduit 14. Although depicted without baffles, the vertical reaction zone can contain open end tubes above the grid for maintaining hydraulic constraints, as disclosed in U.S. Pat. No. 4,251,484 (Daviduk and Haddad). Optionally, a variety of horizontal baffles may be added to limit axial mixing in the reactor. Thermodynamic conditions in the reaction vessel can be controlled by adjusting feed temperature, catalyst temperature and rate, or by heat exchange means 16. In reactor configuration shown the heat exchanger tubes can function as dummy tubes to limit mixing in the reactor.

Provision is made for withdrawing catalyst from above grid 12 by conduit means 17 provided with flow control valve means to control passage via air lift line 18 to the catalyst regeneration system in vessel 20 where coked catalyst particles are oxidatively regenerated in contact with air or other regeneration gas at high temperature. In order to add sufficient heat to the catalytic reaction zone 10, energy may be added by combustion of flue gas or other fuel stream in the regenerator Regenerated catalyst is returned to the reactor fluid bed 10 through conduit means 22 provided with flow control valve means. The hot regenerated catalyst is charged to the catalyst bed sufficiently below the upper interface to achieve good mixing in the fluid bed. The rate of flow for regenerated catalyst may be adjusted to provide the degree of thermal input requied for effecting endothermic conversion, and the rate will depend upon the amount and composition of the alkane components Initial fluidization is achieved by forcing a lift gas upwardly through the catalyst. A light gas, with or without diluent or recycle, may be charged at a bottom portion of the reactor beneath grid 12. Pressurized liquid feedstock is introduced above reactant distributor grid 12, and pumped to one or more spray nozzle means. The liquid is dispersed into the bed of catalyst thereabove at a velocity sufficient to form a generally upwardly flowing suspension of atomized liquid reactant with the catalyst particles and lift gas.

Advantageously, the liquid diene-containing reactant feed is injected into the catalyst bed by atomizing the pressurized liquid feedstream to form readily dispersible liquid particles having an average size of 300 microns or less. This contributes to rapid vaporization of the liquid at process pressure. Exothermic conversion provides sufficient heat to vaporize the liquid quickly, thus avoiding deleterious liquid phase reactions of the diene components, which tend to form carbonaceous deposits such as heavy coke, gums, etc.

Cyclone catlyst particle separator means may be positioned in an upper portion of the reactor vessel. The product effluent separated from catalyst particles in the cyclone separating system then passes to effluent separation system 30. The product effluent is cooled and separated to recover $C_5^+$ liquid hydrocarbons, gaseous recycle or offgas, along with any byproduct water or catalyst fines carried over. A portion of the light gas effluent fraction may be recycled by compressing to form a motive gas for the liquid feed or recycle for use as lift gas. The recovered hydrocarbon product comprising $C_5^+$ olefins and/or aromatics, paraffins and naphthenes is thereafter processed as described hereafter to provide a desired aromatic product.

Atomization of the pressurized liquid reactant feedstream 1 can be achieved by known techniques, such as liquid spray nozzles, motive gas, ultra sonics, etc. A suitable nozzle can comprise a concentric feed liquid projection device. The nozzle may be mounted onto the vessel internal structure. A motive fluid supplied under pressure through conduit drives the pressurized liquid flowing from the nozzle for injection into the reaction vessel at sufficient velocity to induce a fine vertically directed spray of atomized liquid having a particle size in the range of about 30 to 300 microns, preferably about 50 microns. The number and arrangement of nozzles will depend upon the cross sectional area of the fluidized bed and fluidization characteristics of the gas-solid-liquid mixture. The mixture fluid may be an inert material, nitrogen, lower aliphatic gas, stream, etc.

Thermal insulation of the liquid diene-containing feedstream from the hot reaction medium in the reaction vessel can be achieved by applying to the liquid feed conduit a layer of thermal insulation, such as a ceramic shield or the like. Jacketed conduits with heat adsorbing fluid may also be suitable.

Optimized process conditions the turbulent bed has a superficial vapor velocity of about 0.3 to 2 meters per second (m/sec). At higher velocities entrainment of fine particles may become excessive and beyond 10 m/sec the entire bed may be transported out of the reaction zone. At lower velocities, the formation of large bubbles of gas voids can be detrimental to conversion. Even fine particles cannot be maintained effectively in a turbulent bed below about 0.1 m/sec.

A convenient measure of turbulent fluidization is the bed density. A typical turbulent bed has an operating density of about 100 to 500 kg/m$^3$, preferrably about 300 to 500, measured at the bottom of the reaction zone, becoming less dense toward the top of the reaction zone due to pressure drop and particle size differentiation. This density is generally between the catalyst concentration employed in dense beds and the dispersed transport systems. Pressure differential between two vertically spaced points in the reactor column can be measured to obtain the average bed density at such portion of the reaction zone. For instance, in a fluidized bed system employing ZSM-5 particles having a clean apparent density of 1.06 gm/cc and packed density of 0.85, an average fluidized bed density of about 300 to 500 kg/m$^3$ is satisfactory.

By virtue of the turbulence experienced in the turbulent regime, gas-solid contact in the catalytic reactor is improved, providing substantially complete conversion, enhanced selectivity and temperature uniformity. One main advantage of this technique is the inherent control of bubble size and characteristic bubble lifetime. Bubbles of the gaseous reaction mixture are small, random and short-lived, thus resulting in good contact between the gaseous reactants and the solid catalyst particles.

A significant difference between the process of this invention and conversion processes of the prior art is that operation in the turbulent fluidization regime is optimized to produce high octane $C_5^+$ liquid in good yield. The weight hourly space velocity and uniform contact provides a close control of contact time between vapor and solid phases, typically about 3 to 25 seconds. Another advantage of operating in such a mode is the control of bubble size and life span, thus avoiding large scale gas by-passing in the reactor. The process of the present invention does not rely on internal baffles in the reactor for the purpose of bubble size control such as the baffles which are employed in the prior art dense bed processes discussed above.

As the superficial gas velocity is increased in the dense bed, eventually slugging conditions occur and with a further increase in the superficial gas velocity the slug flow breaks down into a turbulent regime. The transition velocity at which this turbulent regime occurs appears to decrease with particle size. The turbulent regime extends from the transition velocity to the so-called transport velocity, as described by Avidan et al in U.S. Pat. No. 4,547,616 and by Tabak et al. in U.S. Pat. No. 4,579,999, incorporated herein by reference. As the transport velocity is approached, there is a sharp increase in the rate of particle carryover, and in the absence of solid recycle, the bed could empty quickly.

Several useful parameters contribute the fluidization in the turbulent regime in accordance with the process of the present invention. When employing a ZSM-5 type zeolite catalyst in fine powder form such a catalyst should comprise the zeolite suitably bound or impregnated on a suitable support with a solid density (weight of a representative individual particle divided by its apparent "outside" volume) in the range from 0.6–2 g/cc, preferably 0.9–1.6 g/cc. The catalyst particles can be in a wide range of particle sizes up to about 250 microns, with an average particle size between about 20 and 100 microns, preferably in the range of 10–150 microns and with the average particle size between 40 and 80 microns. When these solid particles are placed in a fluidized bed where the superficial fluid velocity is 0.3–2, operation in the turbulent regime is obtained. The velocity specified here is for an operation at a total reactor pressure of about 100 to 300 kPa. Those skilled in the art will appreciate that at higher pressure, a lower gas velocity may be employed to ensure operation in the turbulent fluidization regime.

The reactor can assume any technically feasible configuration, but several important criteria should be considered. The bed of catalyst in the reactor can be at least about 5-20 meters in height, preferably about 7 meters. Fine particles may be included in the bed, especially due to attrition, and the fines may be entrained in the product gas stream. A typical turbulent bed may have a catalyst carryover rate up to about 1.5 times the reaction zone inventory per hour. If the fraction of fines becomes large, a portion of the carryover can be removed from the system and replaced by larger particles. It is feasible to have a fine particle separator, such as a cyclone disposed within the reactor shell to recover catalyst carryover and return this fraction continuously to the bottom of the reaction zone for recirculation at a rate of about one catalyst inventory per hour. Optionally, fine particles carried from the reactor vessel entrained with effluent gas can be recovered by a high operating temperature sintered metal filter.

This process can be used with any process stream which contains sufficient liquid olefins and dienes and is substantially free of deleterious oxygenates and sulfur compounds. Experimental runs are performed using a ZSM-5 catalyst to demonstrate the inventive process. The fluidized bed unit can be operated over a wide range of process variables and catalyst activity.

Reactor Operation

A typical single pass reactor unit employs a temperature-controlled catalyst zone with indirect heat exchange and/or adjustable gas quench, whereby heat can be removed or added, depending on the exothermicity or endothermicity of the reaction which in turn depends on the relative concentrations of olefin and paraffins in the feed. The reaction temperature can be carefully controlled in the usual operating range of about 315° C. to 650° C., preferably at average reactor temperature of 425° C. to 580° C. Energy conservation in the system may utilize at least a portion of the reactor exotherm heat value by exchanging hot reactor effluent with feedstock and/or recycle streams. Optional heat exchangers may recover heat from the effluent stream prior to fractionation. For highly endothermic reactions (high alkane concentration in the feed) additional heat can be supplied to the reactor from the regenerator. Various fuels can be burned in the regenerator to raise the temperature of the catalyst. It is preferred to operate the olefin conversion reactors at moderate pressure of about 100 to 3000 kPa (atmospheric to about 400 psig). The weight hourly space velocity (WHSV, based on total olefins in the fresh feedstock) usually is about 0.1-5 WHSV. In order to prevent premature non-catalytic reaction of the dienes, it is desirable to maintain reactant liquid feedstream temperature below about 180° C. (350° F.) until injection into the fluidized bed. Appropriate thermal insulation or quenching of the feedstream to the injection point can largely prevent gum and coke formation in the liquid phase prior to catalysis.

Figure 2:
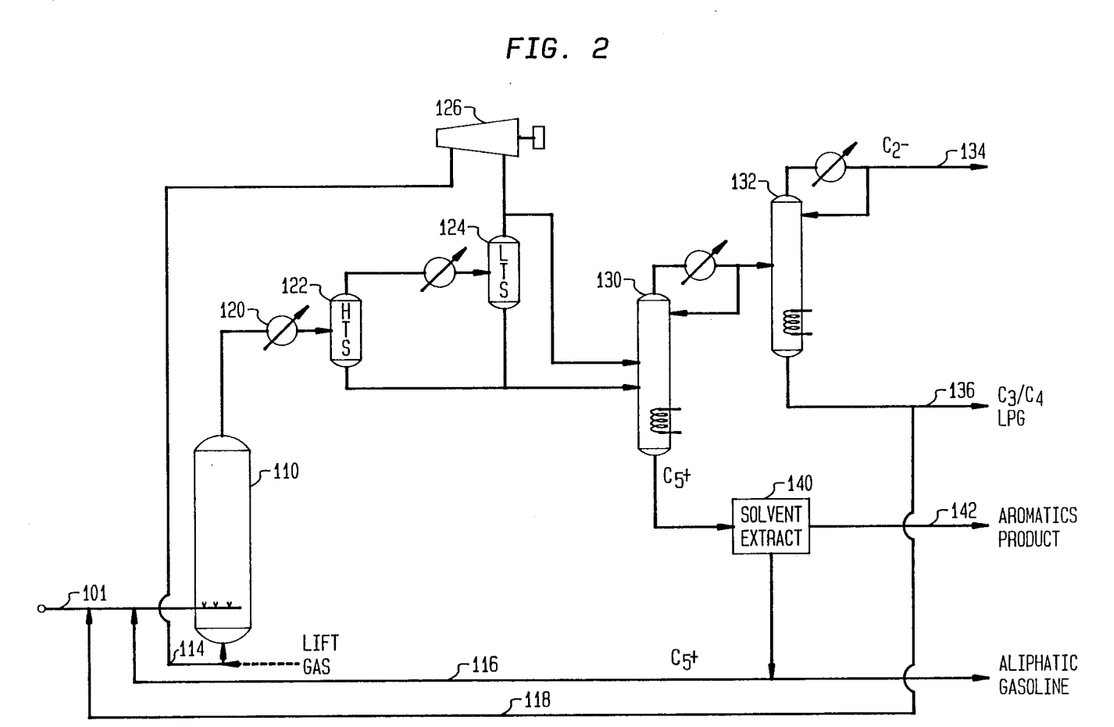
FIG. 2 is process flow sheet for converting olefin feedstock to aromatics-rich product, showing unit operations for reaction, effluent separation, and system equipment.

In FIG. 2, the feedstock stream 101 is injected into reactor vessel 110 containing the fluidized bed of catalyst, along with fluidizing gas stream 114 and recycle streams 116, 118. Reactor effluent is cooled in heat exchanger 120 and partially separated in a series of phase separation drums 122 (high temperature separator) and 124 (low temperature separator). A light gas stream may be recovered from LTS 124, pressurized in compressor 128, and recycled via conduit 114 to comprise at least a portion of the lift gas. Condensed liquid from the separators 122, 124 is fed to a debutanizer tower 130, along with a portion of the LTS ovrhead vapor. Debutanizer overhead vapor is further fractionated by deethanizer tower 132 from which offgas stream 134 is recovered. This light hydrocarbon stream may be employed as fuel gas in the regenerator vessel. Deethanizer liquid bottoms, rich in $C_3$-$C_4$ LPG alkanes, may be recovered via line 136 as product or recycled for further conversion via conduit 118 to reactor 110. The $C_5$+ liquid from the debutanizer 130 is passed to a liquid-liquid extraction unit 140 for recovery of the aromatics components with a selective solvent, such as sulfolane, etc. Following fractionation of the solvent phase, an aromatics product stream 142 is recovered, containing at least 50% BTX. The $C_5$+ aliphatics components may be recovered as a product gasoline stream; however, it is advantageous to recycle this stream for further conversion to increase the net aromatic product.

EXAMPLE 1

In the present high severity example a $C_4$+ liquid stream is converted to aromatics-rich gasoline in the fluidized bed reactor employing acid ZSM-5 powder catalyst having a fresh alpha value of about 175 at an average conversion temperature about 480° C. (900° F.) and total pressure of about 275 kPa (25 psig). The liquid pyrolysis gasoline feedstock contains about 22 wt. % $C_4$+ mono-alkenes, 27% $C_4$+ dienes (mainly butadienes), 49% $C_4$+ paraffins, 2% aromatics and naphthenes, and less than 1% $C_3$− aliphatics. Following initial heating and fluidization of the powdered catalyst with a heated lift gas (e.g., $C_2$− hydrocarbon), the feedstream is preheated and maintained below 180° C. prior to injection into the bed. After achieving steady state operation at a reaction severity index (R.I.) of about 2, the effluent conversion product (less any lift gas components) comprises the following components: total aromatics content is 34.4 wt. %, including 4.9% benzene (B), 11.8% toluene (T), 14% xylenes (X) and 0.9% ethyl benzene, 2.3% $C_9$ aromatics isomers and 0.5% $C_{10}$ isomers. The nonaromatic fraction contains mainly mono-olefins, paraffins and naphthenes, and the light gas $C_4$− fraction is 13.5% of the conversion product.

Comparative effluent stream for high severity and low severity conversion runs under steady state reactor conditions are shown in Table 1.

TABLE 1

| Products Yield | EXAMPLE 1A High Severity | EXAMPLE B Low Severity |
|---|---|---|
| $H_2$, wt. % | 3.0 | 1.3 |
| $C_1$ | 13.5 | 2.6 |
| $C_2$ | 10.3 | 6.1 |
| $C_3$ | 3.8 | 3.4 |
| $C_4$ | 2.0 | 1.4 |
| $C_5$ Non-Aromatic | — | 50.3 |
| Benzene | 22.1 | 4.9 |
| Toluene | 21.9 | 11.8 |
| Ethyl Benzene | 0.9 | 0.9 |
| Xylene | 15.6 | 14.0 |
| $C_9$ Aromatics | 2.7 | 2.3 |
| $C_{10}$+ | 3.2 | 0.5 |
| Coke | 1.0 | 0.5 |
|  | 100.0 | 100.0 |

Typical olefinic pyrolysis byproduct streams are shown in Table 2.

TABLE 2

Example of Diene-Rich Feedstock (ethane crack byproduct)

| Component | Vol. % |
|---|---|
| $C_3^-$ | 1.0 |
| i-butene | 0.08 |
| 1,3-butadiene | 0.51 |
| t.2,butene | 0.1 |
| c.2,butene | 0.15 |
| 1,2 butadiene | 0.14 |
| 3m 1 butene | 0.45 |
| isopentane | 5.44 |
| 1,4 pentadiene | 0.6 |
| 1-pentene | 0.63 |
| n-pentane | 1.92 |
| isoprene | 2.3 |
| c,2,pentene | 0.35 |
| 2m2butene | 0.45 |
| t,1,3,pentadiene | 1.5 |
| c,1,3,pentadiene | 1.0 |
| cyclopentadiene | 13.7 |
| cyclopentene | 1.7 |
| 2,3 d.m. butane | 1.7 |
| 3mpentene | 0.85 |
| hexane | 0.95 |
| unknown $C_6$ | 1.04 |
| cyclohexane | 3.06 |
| benzene | 34.4 |
| unknown $C_8$ | 3.47 |
| Toluene | 10.1 |
| vinyleydohexene | 0.19 |
| ethylbenzene | 1.29 |
| xylene | 1.01 |
| styrene | 0.3 |
| unknown $C_9^+$ | 6.9 |

The above diene-rich stream example contains $C_6^+$ aromatic hydrocarbons which can be separated before feeding to the reactor. Typical ranges of diene-rich pyrolysis gasoline streams comprised of mainly $C_4-C_6$ hydrocarbons are:

| | Vol. % |
|---|---|
| Dienes | 5–60 |
| Mono-alkenes | 5–30 |
| Aromatics | 1–5* |
| Alkanes | 20–60 |
| Naphthenes | 1–5 |

*can be as high as 60% if $C_6^+$ fraction is not separated.

EXAMPLES 2–4

A series of continuous olefin conversion runs are conducted under oligomerization conditions to upgrade mixtures of ethene, propene, butene and butadiene and to determine the effects of diene concentration on catalyst aging. The control feedstock (Example 2) is compared with diene-containing feeds in Table 3.

TABLE 2

| | Example 2 | Example 3 | Example 4 |
|---|---|---|---|
| Ethene | 0 | 0.7 | 1.8 |
| Propene | 26.8 | 28.1 | 22.9 |
| Butenes | 35.7 | 31.9 | 31.7 |
| 1,3 Butadiene | 0 (control) | 0.8 | 5.1 |
| Alkanes ($C_4^-$) | 37.5 | 38.5 | 38.5 |
| Recycle (mol/mol olefin) | 2.5:1 | 2.5:1 | 2.5:1 |

Figure 3:
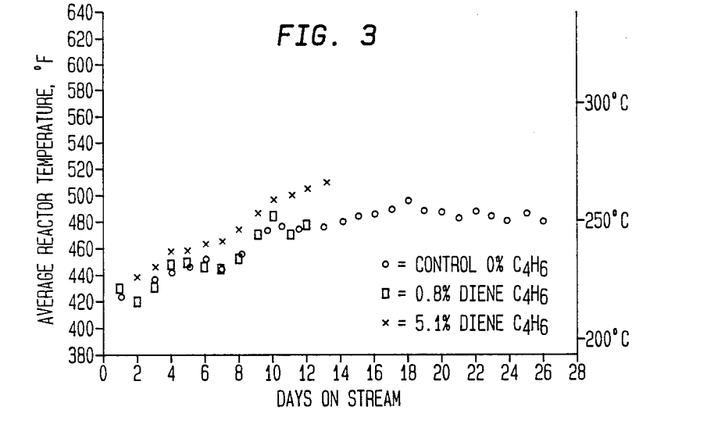
FIG. 3 is a graphic plot for catalytic conversion of $C_2$–$C_4$ olefins showing effects of diene addition on catalyst aging.

The conversion unit is as single bed isothermal reactor employing acid ZSM-5 having a crystal size less than 0.5 microns, together with 35% alumina binder and having a fresh alpha value of about 175. The continuous runs are conducted at about 6600 kPa and weight hourly space velocity (WHSV) of about 0.8 parts olefin feed per part by weight of catalyst per hour. The conversion runs are started at 205° C. (400° F.) and the temperature is increased to compensate for coke deposition, while maintaining total olefin conversion of at least 80%, preferably over 90%. Results of the aging studies are plotted in FIG. 3, with all conversion rates being normalized to 80% conversion to 330° F. for comparison purposes. Selectivity of the conversion product to heavier hydrocarbons is shown in Table 4.

TABLE 3

| | Example 2 | Example 3 | Example 4 |
|---|---|---|---|
| Total Liquid Product, 50% pt, °C. (°F.) | 261/(501) | 259/(498) | 244/(472) |
| Distillate Species (As Cut) | | | |
| 5 wt. %, °C. (°F.) | 232/(434) | 250/(483) | 297(477) |
| 95 wt. % °C. (°F.) | 369/(697) | 383/(722) | 379(715) |
| Gravity, °API | 44.3 | 41.2 | 38.9 |
| Aniline Point | 177 | 184 | 172 |

While the aromatics product content of the control runs average about 2–5%, the 5.1% butadiene feed (Example 4) is upgraded to an aromatics content of 15.5 wt. %, more than 3 times the diene input. The average paraffin content is less than 14% and the liquid dominant product is 70%+olefins and naphthenes.

These results indicate butadiene, at levels of 1 wt. % of less, do not cause significantly increased catalyst aging or lower product selectivity. Typical FCC $C_3/C_4$ olefins from a depropanizer feed stream contain 0.2–0.6 wt. % butadiene which is less than the 0.8 wt. % butadiene concentration that was used in this study. Even at the 5.1 wt. % butadiene level, though catalyst aging was increased, product selectivity to heavier hydrocarbons remainded relatively high.

The flexibility of the fluid bed operating parameters for controlling the reactor temperature under exothermic reaction conditions allows an easy adjustment for achieving the optimal yield structure.

In order to effect fluidization of the catalyst at the bottom of the reactor prior to injection of the liquid feed stream, a lift gas may be employed. This can be an inert diluent or recycled light gas, such as methane, ethane, ethene, propane, etc. Recycle of $C_3^-$ light hydrocarbons may also be desirable under certain circumstances, for instance with unreacted aliphatics which require further conversion. The thermodynamic balance of exothermic olefin oligomerization and endothermic paraffin reactions can have significant impact on the reaction severity conditions.

The use of a fluid-bed reactor in this process offers several advantages over a fixed-bed reactor. Due to continuous catalyst regeneration, fluid-bed reactor operation will not be adversely affected by oxygenate, sulfur and/or nitrogen containing contaminants present in the pyrrolysis byproduct.

While the invention has be shown by describing preferred embodiments of the process, there is no intent to limit the inventive concept, except as set forth in the following claims.

We claim:

1. A continuous process for converting lower olefinic hydrocarbon feedstock to aromatics-rich product by contacting the feedstock in a fluidized bed reaction zone with acidic siliceous zeolite conversion catalyst particles at elevated temperature under exothermic conditions to produce heavier hydrocarbons including gasoline range hydrocarbons comprising:

maintaining a turbulent fluidized bed of catalyst particles by flowing hydrocarbon-containing vapor upwardly through said bed at less than transport velocity; and introducing lower olefinic feedstock comprising at least one $C_4$-$C_6$ diene component into the fluidized catalyst bed in a lower portion thereof to convert feedstock to heavier hydrocarbon rich in aromatic hydrocarbon without substantial thermal diene degradation thereof prior to contacting conversion catalyst particles in the fluidized bed;

separating an aromatics-rich liquid stream from fluidized bed reaction effluent;

extracting aromatics components from the liquid stream and recovering a second liquid stream rich in $C_5$+ aliphatics hydrocarbons;

recycling at least a portion of the second $C_5$+ aliphatics-rich stream to the fluidized bed reaction zone; and recovering an aromatics product stream.

2. The process of claim 1 wherein the olefinic feed comprises about 5 to 90 wt. % $C_4$+ mono-olefin and 1 to 50 wt. % conjugated unsaturated diolefins, wherein the fluidized bed is maintained at an average temperature of about 315° C. to 650° C., wherein the catalyst comprises medium pore shape selective metallosilicate; and wherein the net yield of aromatic product comprises at least 30 wt % of the olefin components of the feedstock.

3. The process of claim 2 wherein said feedstock consists essentially of liquid pyrolysis gas byproduct of hydrocarbon pyrolysis, wherein the catalyst comprises zeolite having the crystalline structure of ZSM-5, wherein the superficial vapor velocity through the fluidized bed is about 0.2 to 3 meters/sec and liquid feedstock is introduced at super-atmosphere pressure as an atomized liquid.

4. A process for continuous conversion of diene-containing aliphatic hydrocarbon feedstock to heavier hydrocarbon products wherein the feedstock is contacted at elevated temperature under high severity reaction conditions with a fluidized bed of acidic zeolite fine catalyst particles, comprising the steps of:

maintaining the fluidized catalyst bed in a vertical reactor having a turbulent reaction zone by passing vapor upwardly through the reaction zone at a velocity greater than dense bed transition velocity to a turbulent regime and less than transport velocity for the average catalyst particle;

feeding a continuous stream of feedstock into the reaction zone, said feedstream comprising sufficient $C_3$+ alkanes to require net endothermic reaction conditions;

withdrawing a portion of coked catalyst from the reaction zone, oxidatively regenerating the withdrawn catalyst, heating the catalyst substantially above process temperature in the fluidized bed reactor, and returning hot regenerated catalyst to the reactor zone at a rate to control catalyst activity and reaction temperature under conditions of reaction severity to effect feedstock conversion to an aromatics-rich hydrocarbon effluent stream;

separating an aromatics-rich product from the fluidized bed effluent stream; and recovering a recycle stream comprising $C_5$+ aliphatic hydrocarbons from the fluidized bed effluent stream for further conversion in the fluidized bed to increase aromatics product yield.

5. The process of claim 4 wherein the superficial feedstock vapor velocity is about 0.3–2 m/sec; the reaction temperature is about 315° to 650° C.; the weight hourly feedstock space velocity (based on total olefin) is about 0.1 to 5; propane:propene weight ratio about 0.7:1 to 5:1; and the average fluidized bed density measured at the reaction zone bottom is about 300 to 500 kg/m$^3$.

6. The process of claim 4 wherein the catalyst consists essentially of a medium pore pentasil zeolite having an apparent alpha value of about 15 to 250, and average particle size of about 20 to 100 microns, including at least 10 weight percent fine particles having a particle size less than 32 microns.

7. The process of claim 6 wherein the catalyst particles comprise about 5 to 90 weight percent ZSM-5 zeolite having a crystal size of about 0.01–2 microns.

8. The process of claim 4 wherein said feedstock consists essentially of $C_4$-$C_6$ hydrocarbon liquid containing about 5 to 50 wt % $C_4$-$C_6$ conjugated unsaturated dienes and substantially free of deleterious oxygenates and sulfur compounds.

9. The process of claim 8 wherein the olefin partial pressure is at least 50 kPa and wherein propane:propene molar ratio in the hydrocarbon product is maintained at about 0.2:1 to 50:1 in the substantial absence of added propane.

10. The process of claim 4 wherein said feedstock consists essentially of liquid pyrolysis gasoline byproduct of hydrocarbon pyrolysis, wherein the catalyst comprises zeolite having the crystalline structure of ZSM-5, wherein the superficial vapor velocity through the fluidized bed is about 0.2 to 3 meters/sec and feedstock is introduced predominantly in liquid phase above process reactor pressure and at a temperature not greater than about 180° C.

11. The process of claim 10 wherein the liquid feedstock is atomized to an average particle size not greater than about 300 microns.

12. The process of claim 4 wherein a portion of light hydrocarbon gas recovered from reactor effluent is recycled to the reactor as a fluidizing lift gas and is distributed to the bottom of the reactor through a grid below the liquid feed.

13. The process of claim 4 wherein the catalyst is modified with a hydrogenation-dehydrogenation metal component to increase aromatics production.

* * * * *